United States Patent [19]

Johnson

[11] Patent Number: 5,002,575
[45] Date of Patent: Mar. 26, 1991

[54] BONE IMPLANT PROSTHESIS
[75] Inventor: Wesley Johnson, Minnetonka, Minn.
[73] Assignee: Orthomet, Inc., Minneapolis, Minn.
[21] Appl. No.: 342,283
[22] Filed: Apr. 24, 1989

Related U.S. Application Data

[62] Division of Ser. No. 151,108, Feb. 1, 1988, Pat. No. 4,851,008.
[51] Int. Cl.⁵ ............................ A61F 2/28; B23H 7/18
[52] U.S. Cl. ..................................... 623/16; 623/66; 219/69.17
[58] Field of Search ............... 219/69.2, 69.17, 69.15; 623/66, 16, 11

[56] References Cited

U.S. PATENT DOCUMENTS

| | | | |
|---|---|---|---|
| 4,096,371 | 6/1978 | Lozon | 219/69.17 |
| 4,229,636 | 10/1980 | Izari | 219/69.17 |
| 4,310,742 | 1/1982 | Pfau | 219/69.17 |
| 4,608,476 | 8/1986 | Shimizu | 219/69.17 |
| 4,673,409 | 6/1987 | Van Kampen | 623/23 |
| 4,721,838 | 1/1988 | Abdukarimov et al. | 219/69.17 |
| 4,752,294 | 6/1988 | Lundgren | 623/66 |
| 4,772,368 | 9/1988 | Rabian | 219/69.2 |

Primary Examiner—David J. Isabella
Attorney, Agent, or Firm—James R. Haller; Gregory P. Kaihoi; Mary P. Bauman

[57] ABSTRACT

A bone implant prosthesis having an outer stress-free surface and a subsurface carried generally beneath and parallel to the outer surface for bearing tensile stresses. The prosthesis of the invention includes a plurality of slots undercutting the outer surface of the prosthesis thus forming a stress bearing subsurface to free the outer surface from being subjected to substantial stresses. The stress-free outer surface is readily adaptable to receive a porous coating to enhance bone ingrowth without decreasing the stress resistance characteristics of the prosthesis.

10 Claims, 4 Drawing Sheets

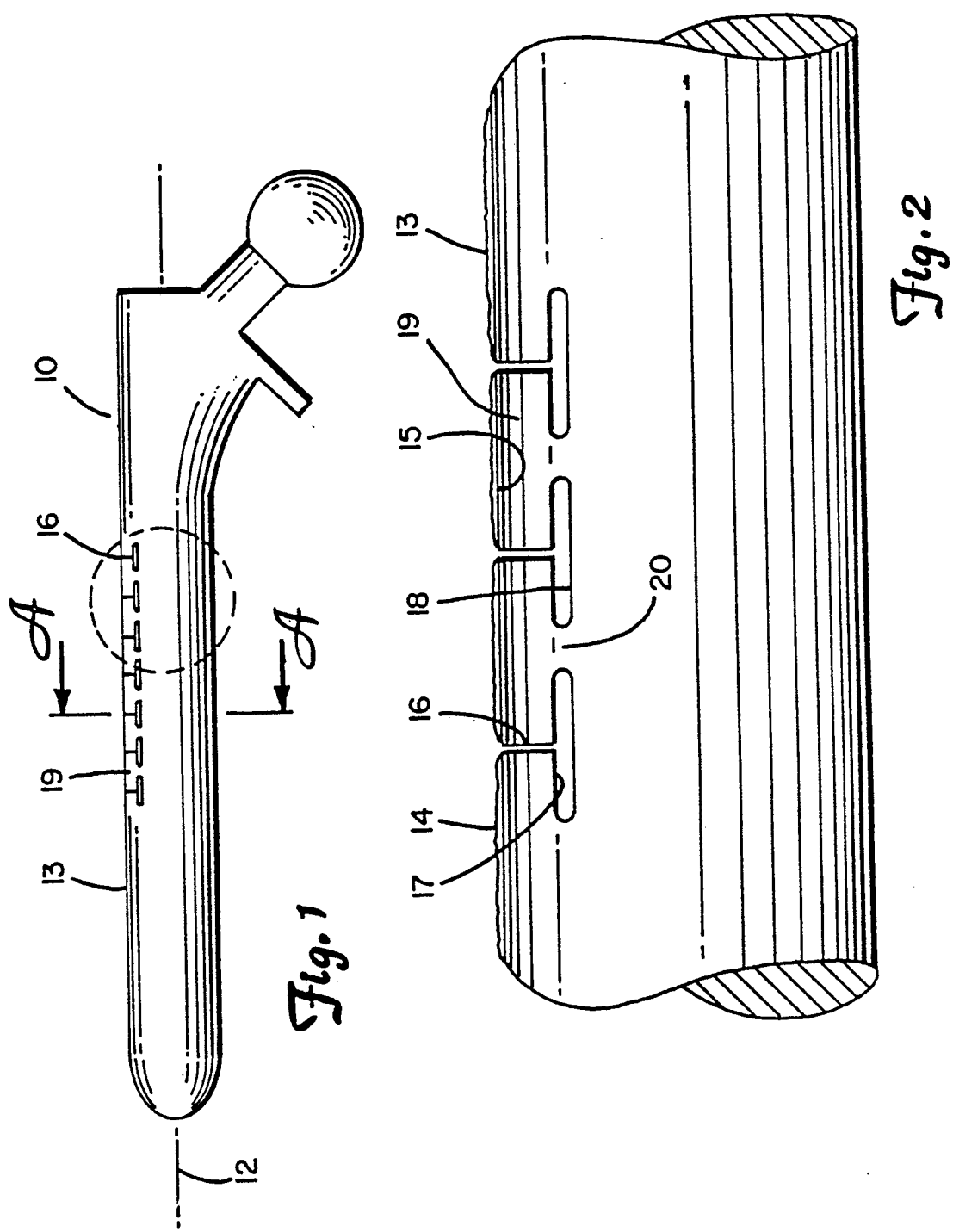

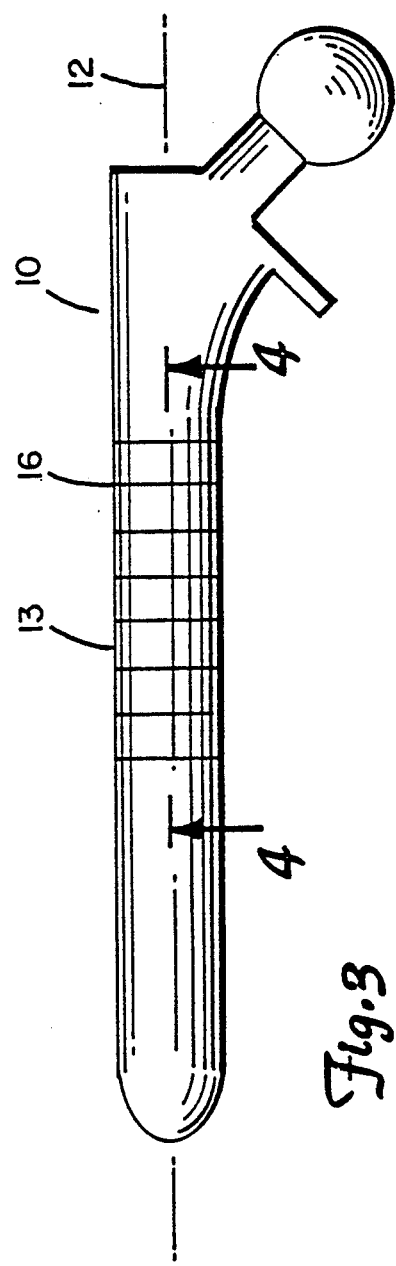
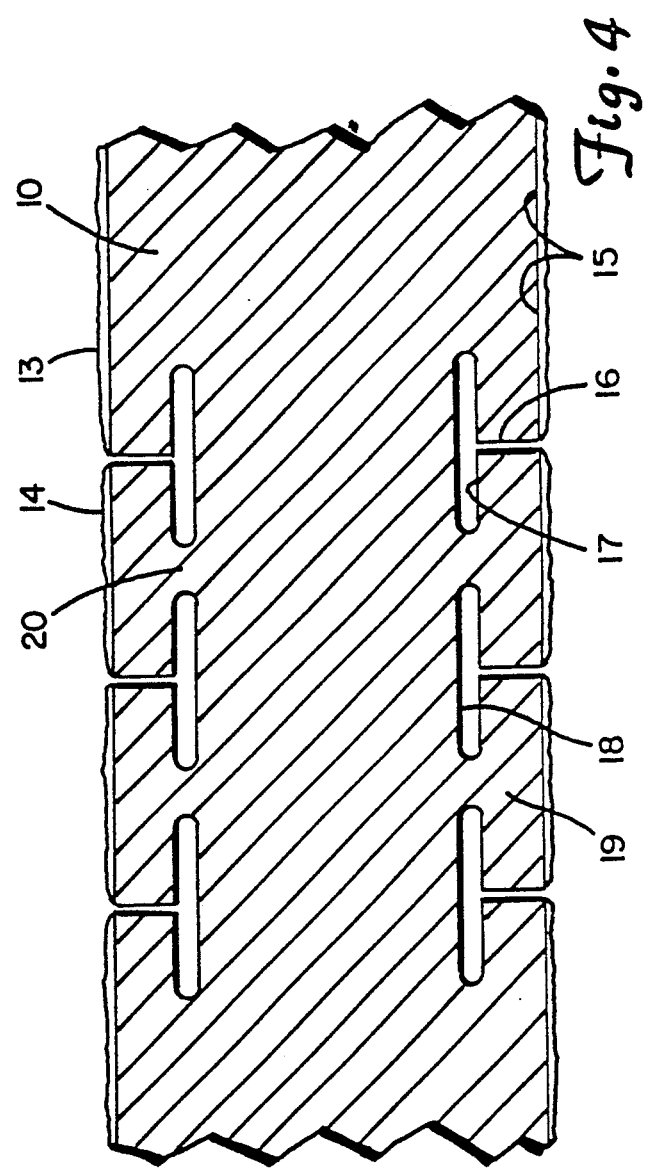

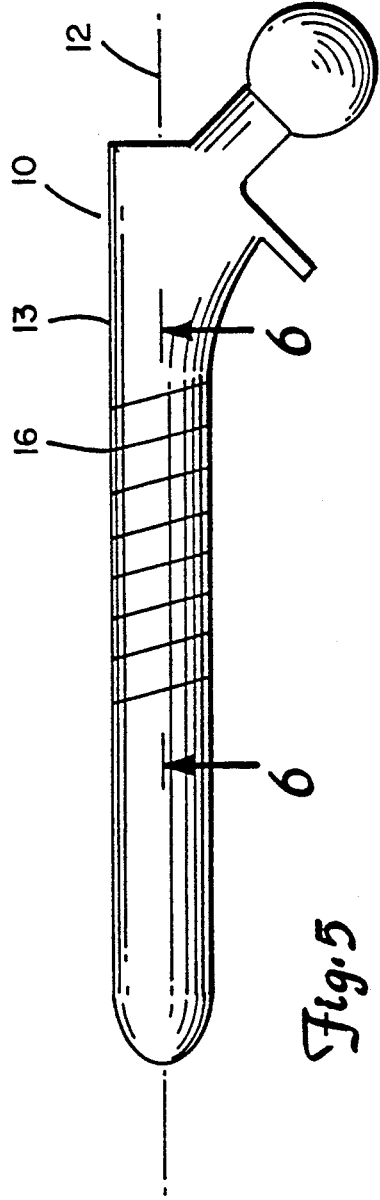
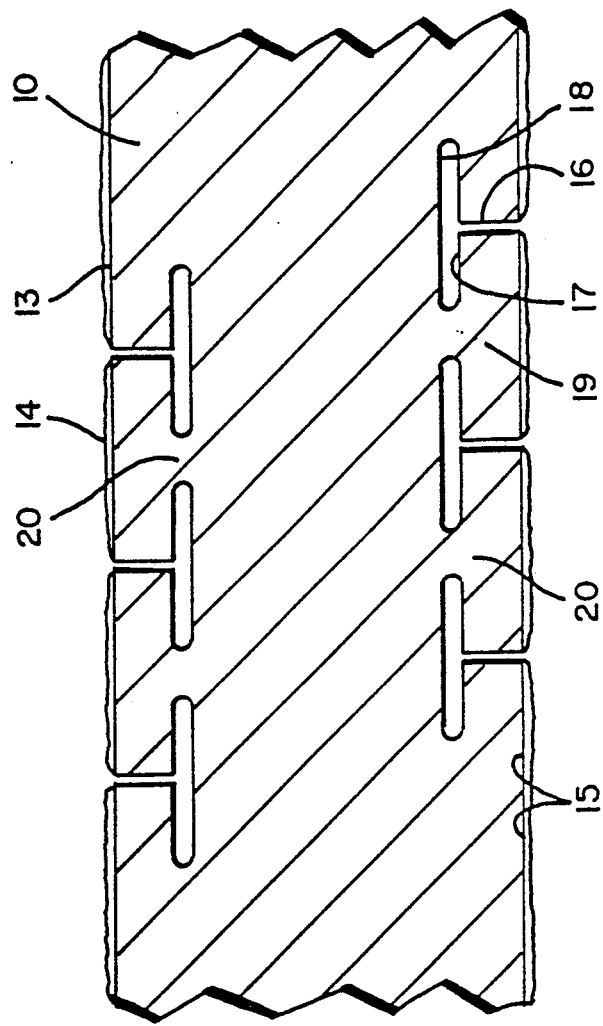
Fig. 5
Fig. 6

BONE IMPLANT PROSTHESIS

This is a divisional of co-pending U.S. patent application Ser. No. 151,108, filed on Feb. 1, 1988 now U.S. Pat. No. 4,851,008.

FIELD OF THE INVENTION

The invention relates to bone implant prostheses and, more particularly, to bone implant prostheses which are capable of withstanding the application of large stresses.

BACKGROUND OF THE INVENTION

It has been common in the past, in the case of serious bone fractures in which simple resetting is contraindicated, to replace all or part of the bone with a suitable implant generally made of titanium or another metal. An example of an implant of this type is a femoral implant which includes a stem for insertion in the intermedullary canal of the femur, a neck portion at an angle to the stem, and a capitulum carried at the end of the neck. Because of the shape of the prosthesis and the high-stress location in which it is employed, its outer or lateral surface is subjected to substantial bending stresses, putting the outer surface in tension, during each step that a patient takes. Since titanium can withstand repeated cycles (i.e. $10^8$ cycles) of stress of about 80,000 psi, smooth titanium implants are generally used for this type of application.

It is often preferable to render porous the outer surfaces of the prosthesis by applying a thin coating of metallic beads to enhance the ingrowth of bone material. The porous metallic bead coatings are generally sintered onto the surface of the prosthesis utilizing relatively high temperatures. The combination of the high temperature and the application of the beads causes some of the beads to penetrate the surface of the prosthesis forming notches or stress-concentration sites. These stress concentration sites are likely locations from which cracks may form in the outer surface of the prosthesis as it is continuously cycled in tension. Cracks are very undesirable because they can significantly weaken the prosthesis and can cause the prosthesis to fail.

The characteristics of the surface of the prosthesis affects the amount of stress that the prosthesis can withstand at a given number of stressing cycles. The amount of stress that a prosthesis can withstand, while staying within its elastic limit, at a large number of cycles of stress (e.g., $10^8$ cycles) is referred to as the fatigue endurance limit. Titanium and titanium alloys are particularly notch-sensitive in that when prostheses formed of these materials are notched in stressed areas, the fatigue endurance limit may be significantly reduced.

It is preferrable to have bone implant prostheses having porous coatings because bone ingrowth into the coatings can significantly strengthen the bone-prosthesis bond. However, it has been found that prostheses of the type described above are prone to premature failure due to the abundant stress concentration sites and their tendency to promote cracking. In general, prostheses with porous outer surfaces can withstand repeated (e.g., $10^8$) tensile stress cycles of only about 20,000 psi.

The metallic bead coatings are further preferred because they have elastic qualities that are somewhat similar to those of the metal upon which they are placed. This feature enables both the metal implant and the thin coating to stretch and flex together without interrupting the bond between them.

Ceramic porous coatings are also used, but since ceramic materials do not possess good elastic characteristics, slight bending of the femoral implant (such as that caused by normal walking) may crack and loosen the ceramic beaded surface.

It is desired to have a bone implant prosthesis with a porous outer surface possessing the strength to withstand the repeated stresses of normal implanted use.

SUMMARY OF THE INVENTION

The invention relates to a bone implant prosthesis for the surgical reconstruction and repair of bone fractures and other abnormalities in bone structure. The prosthesis comprises a body portion having a stress-free outer surface and a stress-bearing subsurface generally parallel to and spaced beneath the outer surface. A series of generally parallel spaced slots extend into the prosthesis, the slots having widened lower portions which form the stress-bearing subsurface. A discontinuous plane surface is formed by the floor of the slots which, when the prosthesis is stressed, becomes the plane bearing the maximum tensile stress. In this configuration, the outer surface of the prosthesis is essentially stress-free and therefore may be provided with a porous coating without weakening the stress bearing characteristics of the prosthesis.

BRIEF DESCRIPTION OF THE DRAWINGS

FIG. 1 is an elevation view of the bone implant prosthesis of the invention;

FIG. 2 is a detailed view of the portion of FIG. 1 within the dashed circle;

FIG. 3 is an elevation view of an alternative embodiment of the invention showing slots extending around the circumference of the prosthesis;

FIG. 4 is a cross-sectional view of the prosthesis of FIG. 3 taken along line 4—4 thereof;

FIG. 5 is an elevation view of an alternative embodiment of the invention showing spirally arranged slots about the circumference of the prosthesis; and FIG. 6 is a cross-sectional view of the prosthesis of FIG. 5 taken along line 6—6 thereof.

DETAILED DESCRIPTION OF THE PREFERRED EMBODIMENTS

Figure 1A:
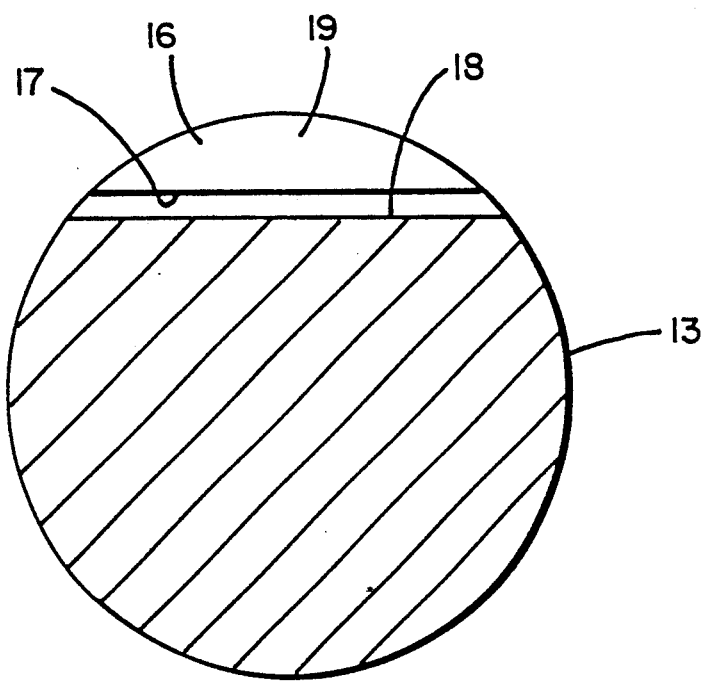
FIG. 1A is a cross-sectional view of the prosthesis of FIG. 1 taken along line A—A thereof.

The bone implant prosthesis of the invention is of the type intended to be surgically implanted into living tissue for reconstruction of body structure. The device of the invention is particularly suited for but not limited to use as a femoral implant due to its favorable stress bearing characteristics, as that type of implant prosthesis is generally subjected to large cyclic stresses.

The invention comprises a bone implant prosthesis (10) having a stress-free outer surface (13) upon which may be applied a porous coating (14), and a stress-bearing subsurface (18). As shown in FIGS. 1 and 2, the stress-free outer surface (13) is created by undercutting the outer surface (13) with a series of slots (16). The slots (16) are preferably "T" shaped and spaced such that a minimal metal ligament (20) is present between adjacent slots (16). The result is an outer surface (13) comprised of a plurality of relatively large sections of material (19) suspended generally above a lower subsurface (18) by thin ligaments (20). In this configuration, tensile stresses applied to the prosthesis (10) are borne by the subsurface (18) and are not transferred to the outer surface (13).

Preferably, the slots (16) are designed so that, under extreme loading conditions, the portion of the slot (16) extending to the outer surface (13) of the prosthesis (10) is adequately sized to prevent adjacent outer surface portions (19) from contacting one another. If the outer surface portions (19) were allowed to contact one another, the outer surface (13) would be stressed while the portions (19) were in contact. This contact is undesirable because stressing of the outer porous surface (13) may cause cracks to develop. Therefore, it is desirable to utilize slots (16) of adequate width to prevent the external surface portions (19) from contacting one another even under extreme loading conditions.

The slots (16) are preferably formed by passing a generally "T" shaped electrode through the surface of the prosthesis (10) to a depth of approximately one tenth of an inch. The electrode is supplied with an electrical current having a high voltage which substantially melts a path through the prosthesis (10). The electrode may be moved in a straight line path through several lateral surfaces of the prosthesis (10) thus forming straight slots (16) through the prosthesis (10) as shown in FIGS. 1, 1A and 2.

The slots (16) are preferably T-shaped in cross-section and, in one embodiment, are straight, formed as chords across the curved surface of the prosthesis (10). The cross bars of the T's are generally spaced beneath the outer surface (13) of the body and have a widened portion (17) defining a stress-bearing sub-surface (18). Perfect alignment or parallelism of slots (16) is not required, nor must the slots (16) be uniformly spaced from one another.

Alternatively, the electrode may be inserted into the prosthesis (10) in a radial direction with the longitudinal portion directed perpendicular to the axis (12) of the prosthesis (10) and rotated approximately 90 degrees when it reaches a desired depth beneath the surface (13). The prosthesis (10) may then be rotated through at least 360 degrees to cut a slot (16) substantially entirely around the perimeter of the prosthesis (10) spaced from the outer surface (13). The electrode could then be rotated 90 degrees and removed in a radial direction from the prosthesis (10). A plurality of identical slots (16) may be made, spaced from one another by a predetermined distance, creating a stress-free sub-surface (18) about the perimeter of the prosthesis (10). This procedure would create a smooth subsurface (18) comprised of a plurality of slots (16) that could be subjected to substantial stresses thus allowing the external periphery of the prosthesis (10) to carry a porous coating (14). A prosthesis of the type described above is shown in FIGS. 3 and 4.

In another embodiment of the invention, shown in FIGS. 5 and 6, the slot (16) may be embodied as a single helical channel extending around the perimeter of the prosthesis (10), spaced from the outer surface (13), along a portion of the length of the prosthesis (10).

There are many useful applications for these concepts. One of the applications involves the addition of a porous coating (14) (e.g., plasma spray or sintered bead) to the stress-free outer surface (13) that is created. Some of the porous coatings create small stress concentration sites (15) in the titanium surface of the prosthesis. Applying the coating to a stress-free surface neutralizes the notch sensitivity of the titanium, thereby dramatically increasing the endurance limit for repeated stressings of the implant.

The stress-free surface is readily acceptable for application of a hydroxylapatite (HA) coating. HA coatings are becoming very popular within the orthopedic community. One of the major problems in utilizing such coatings in the past has been the propensity for the coating to separate from the substrate. This separation may be due, in part, to tensile stresses within the substrate which create a strain gradient between the coating and the substrate.

The creation of a stress-free surface on the implant may favorably enhance osteointegration (bone ingrowth or bone ongrowth). One of the major problems in total joint replacement is the presence of a fibrocartilaginous layer between the implant and the bone. In some cases, this layer is the result of a dramatic strain gradient between implant and supporting bone structure. Such a strain gradient creates micromotion at the interface. This micromotion promotes fibrous tissue formation. In the case of severe micromotion, fibrous tissue formation may be progressive, leading to implant loosening and failure.

In various embodiments of the invention, the depth of the slots (16), or stress neutralizing channels, may be varied to alter the structural stiffness of the implant. The structural stiffness could then be optimized along the length of the stem to create a more uniform (i.e., physiological) stress pattern within the supporting bone structure.

Some of the potential implant uses for this invention include hip stem, acetabular cup, total knee (tibial tray and femoral component), spinal fixation rods and plates, trauma plates and intramedullary rod implants.

While a preferred embodiment of the present invention has been described, it should be understood that various changes, adaptations and modifications may be made therein without departing from the spirit of the invention and the scope of the appended claims.

What is claimed is:

1. A method of undercutting an outer surface of an implant process to create a subsurface, the method comprising the steps of providing an electrode having a longitudinal portion and a cross bar, providing a charge to the electrode, and passing the electrode through the prosthesis to form a plurality of parallel, enlarged subsurface slots spaced inwardly from the outer surface, said slots having floor portions defining a stress-bearing discontinuous smooth subsurface spaced beneath the outer surface.

2. The method of claim 1 wherein the slots are generally "T" shaped and the cross-bar of the "T" forms a subsurface carried beneath and parallel to the outer surface.

3. The method of claim 1 wherein the prosthesis has an arcuate surface and wherein the electrode is passed through the prosthesis to define slots which are generally linear and spaced laterally, each slot being formed as a chord across said arcuate surface.

4. The method of claim 1 wherein the electrode is passed through the prosthesis to define slots which are spaced laterally and extend around the prosthesis spaced inwardly from the outer perimeter.

5. The method of claim 1 wherein the electrode is passed through the prosthesis to define slots which are spaced laterally and extend spirally about the prosthesis spaced inwardly from the outer surface of the prosthesis.

6. Method of relieving stress concentrations from the outer surface of a bone implant prosthesis that is subjected to stress during use, the method comprising the steps of providing a generally T-shaped electrode, supplying to the electrode an electrical current, and passing the electrode beneath the surface of the prosthesis to form substantially parallel, generally T-shaped slots therein, the slots being spaced from one another and having widened floor portions together defining a stress-bearing discontinuous smooth subsurface spaced beneath the outer surface.

7. The method of claim 6 wherein said prosthesis includes an arcuate surface and, wherein said electrode is passed through said prosthesis to define generally linear slots, each slot forming a chord across said arcuate surface.

8. The method of claim 6 wherein said prosthesis includes an arcuate surface and wherein said electrode is passed through said prosthesis to define generally arcuate slots positioned at a substantially uniform depth below said surface, said stress-bearing subsurface being generally parallel to the surface of the prosthesis.

9. The method of claim 8 wherein said prosthesis has an axis and said T-shaped electrode includes a longitudinal portion and a cross bar, the step of passing the electrode beneath the surface of the prosthesis further comprising the steps of orienting the longitudinal portion of the electrode generally perpendicular to said axis and orienting the cross bar of the electrode substantially perpendicular to, but radially spaced from, said axis; inserting the electrode into the prosthesis to a predetermined depth; rotating the electrode with respect to the prosthesis about said longitudinal portion through an angle of approximately 90°; rotating the prosthesis with respect to the electrode; rotating the electrode with respect to the prosthesis about said longitudinal portion to orient the cross bar substantially perpendicular to but radially spaced from said axis; and removing the electrode from the prosthesis.

10. The method of claim 6 wherein said step of forming generally T-shaped slots further comprises the steps of passing said electrode beneath the surface of the prosthesis to define a single T-shaped slot, removing the electrode from the prosthesis, moving the electrode laterally with respect to the prosthesis, passing the electrode beneath the surface of the prosthesis to define a second T-shaped slot adjacent to the first slot, the first and second slots being substantially parallel to one another.

* * * * *